United States Patent [19]

Montgomery et al.

[11] Patent Number: 4,948,628
[45] Date of Patent: Aug. 14, 1990

[54] METHOD FOR PLASMA TREATMENT OF SMALL DIAMETER TUBES

[75] Inventors: David B. Montgomery; Joel L. Williams, both of Cary, N.C.

[73] Assignee: Becton, Dickinson and Company, Franklin Lakes, N.J.

[21] Appl. No.: 335,476

[22] Filed: Apr. 10, 1989

Related U.S. Application Data

[62] Division of Ser. No. 214,244, Jul. 1, 1988, Pat. No. 4,846,101.

[51] Int. Cl.[5] .............................................. C23C 16/50
[52] U.S. Cl. ......................................... 427/39; 427/38; 427/40; 427/41; 427/237; 427/238; 156/643
[58] Field of Search ....................... 427/38, 39, 40, 41, 427/237, 238; 118/723; 156/345, 643

[56] References Cited

U.S. PATENT DOCUMENTS

| | | | |
|---|---|---|---|
| 4,261,806 | 4/1981 | Asai et al. | 427/40 |
| 4,473,596 | 9/1984 | Beerwald et al. | 427/238 |
| 4,692,347 | 9/1987 | Yasuda | 427/237 |

Primary Examiner—Shrive Beck
Assistant Examiner—Margaret Bueker
Attorney, Agent, or Firm—Richard E. Brown

[57] ABSTRACT

An apparatus for generating a plasma in the lumen of a small diameter tube includes a housing having a diaphragm which separates the housing into a first chamber equipped with a gas inbleed assembly and a second chamber connected to a vacuum source. Parallel plate electrodes in the first chamber are encased in a dielectric which prevents substantially all plasma discharge external of a plasma zone between the electrodes. A conduit maintains gas flow between the chambers. A bore through the dielectric includes the plasma zone and receives the tube to be plasma treated.

A method for treating the luminal wall of a plastic tube includes positioning a tube in the plasma zone, evacuating the chambers, bleeding a gas into the chambers, and delivering radiofrequency power to the electrodes. A long tube may be drawn through the plasma zone, or the dielectric and electrodes may be moved past the tube.

3 Claims, 8 Drawing Sheets

METHOD FOR PLASMA TREATMENT OF SMALL DIAMETER TUBES

This is a division of application Ser. No. 214,244, filed Jul. 1, 1988, now U.S. Pat. No. 4,846,101.

BACKGROUND OF THE INVENTION

1. Field of the Invention.

This invention relates to techniques and implements to facilitate the attachment of cells to a surface, and more specifically relates to an apparatus for plasma treating the lumen wall of a small diameter tube in preparation for cell deposition.

2. Background.

Over the past three decades, vascular grafts have been used extensively to restore blood flow to areas of ischemia, to provide blood flow for hemodialysis patients and for repair of arterial aneurisyms. Such procedures are generally initially successful, but long term prognosis for patients receiving small diameter grafts is not encouraging, principally because grafts of 4 mm or less become occluded over time due to the thrombogenic nature of the graft material.

Extensive investigations have been carried out in attempts to find blood compatible materials for vascular grafts and other biomedical devices. Synthetic plastics are the preferred materials, but even such plastics as polytetrafluoroethylene and the silicone rubbers which are more compatible with blood than most plastics still show thrombogenic characteristics.

The problems of thrombogenicity and occlusion are exacerbated with small diameter grafts. Van Wachem et al., in *Biomaterials* 6, 403 (1985) reported clinical success with polymeric grafts of greater than 4 mm, but that grafts of less than 4 mm gave generally disappointing clinical results due to immediate occlusion. Likewise, Baker et al., in *American Journal of Surgery* 150, 197 (1985) stated that long term patency of large diameter vascular grafts is relatively acceptable, but small diameter (less than 5 mm) grafts exhibit poor long-term patency rates.

The ideal blood surface interface has long been considered to be the naturally occurring human endothelium, and much current research centers on endothelialization procedures. For example, seeding of 4 mm ID diameter polyester vascular grafts with endothelial cells and patency after implantation in dogs is discussed by Belden et al., in *Trans. Am. Soc. Artif. Intern. Organs.* 28, 173 (1982).

Jarrell et al. (Annals of Surgery, 203, 671 (1986)) disclosed a high percentage of firm adherence of endothelial cells to polyester coated with platelet rich-plasma in 10 min., to amnion/collagen coated polyester in 30 min. and to plain polyester in two hours, but that only the amnion/collagen coated surface exhibited complete graft coverage.

Modification of polymeric surfaces by treatment with a variety of plasmas to accomplish various purposes is well known. The term "plasma" is used generally to describe the state of ionized gas. A plasma consists of high energy positively or negatively charged ions, negatively charged electrons as well as neutral species. As known in the art, a plasma may be generated by combustion, flames, physical shock or most often by electrical discharge, such as a corona or glow discharge. In radiofrequency (RF) discharge, a substrate to be treated is placed in a vacuum chamber and gas at low pressure is bled into the system. The gas is subjected to an RF electrical discharge, either capacitive or inductive, which generates an electromagnetic field. Ionization of the gas takes place as a result of absorption of energy from the field giving high energy particles which modify the surface of the substrate.

The extent of substrate surface modification by a plasma is a function of the number and average energy of the particles striking the surface. The energy of charged particles in a plasma is best defined by the ratio (E/p) of the electric field strength E to the background gas pressure p. This ratio is a relative measure of the average energy that an ion or electron can gain between successive scattering collisions with neutral gas molecules. It is evident from the ratio that the energy of a plasma particle can be increased by either increasing the field strength or decreasing the gas pressure. Field strength may be increased by increasing the power of the electrical discharge; this, however, is accompanied by additional heat formation. On the other hand, if the gas pressure is reduced too far, insufficient molecules are present for ionization.

Plasmas have been used to alter surface wettability, static properties and receptivity of a surface to deposition of a layer of an adherent polymeric material. Japanese Patent No. 122529 discloses preparing a surface for graft polymerization by placing a tube in an insulating sheath, activating an inner surface of the tube with an inductively generated plasma and exposing the surface to a polymerizable monomer.

Van Wachem et al., (supra) discloses that endothelial cells can be cultured on glass or glow-discharge treated polystyrene.

Garfinkle et al., in Trans. Am. Soc. Artif. Intern. Organs, 30, 432 (1984) discloses plasma deposition of a fluorocarbon polymer coating onto the luminal surface of 4–5 mm inside diameter porous polyester grafts. In this report, an inductive plasma generated externally of the graft penetrates to the lumen by passing through the pores of the graft. Markedly improved patency for the treated grafts is reported.

Published European Patent Application EP 89-124A discloses plasma treatment of the inside of a plastic tube of 3.5 mm inside diameter by inserting the tube inside an insulating second tube and positioning the electrodes outside of the insulating tube.

In spite of the extensive investigations on antithrombogenic prosthetic devices, the problem of thrombogenicity has not been satisfactorily solved, in particular with respect to small diameter grafts. It is toward the solution of this problem that the current invention is directed.

SUMMARY OF THE INVENTION

An apparatus for modifyinq an interior surface of an article with a plasma includes an electromagnetic field generator inside a housing. The housing has a connection to a vacuum source and a gas inbleed assembly. The generator is connected to an RF power source and is enclosed in a dielectric in all directions except in the direction of a plasma zone adjacent the generator. The plasma zone receives the article to be plasma treated.

In one preferred apparatus of the invention, the housing is a canister having upper and lower chambers separated by a diaphragm wherein the gas inbleed is connected to the upper chamber and the vacuum connection is on the lower chamber. The preferred generator includes a plurality of parallel plate electrodes and the dielectric is a block of high molecular weight polyolefin having a recess in the interior which receives the electrodes. A bore which includes the plasma zone passes through the dielectric and establishes gas communication from the upper chamber through the recess and an aperture in the diaphragm to the lower chamber. A tube to be plasma treated is positioned in the bore and extends from the upper chamber into the lower chamber. A conduit through the diaphragm provides gas communication between the upper and lower chambers. The conduit controls the gas flow from the upper chamber to the lower chamber so that a lower gas pressure may be maintained in the lower chamber. A rod passes through the top wall of the canister and engages the upper end of the tube to be plasma treated so that a long tube may be drawn slowly through the plasma zone between the electrodes.

In another preferred embodiment of the apparatus, the tube is positioned between support rails, and the dielectric having the electrodes disposed therein is drawn laterally along the rails to deliver the plasma to the entire luminal wall of a long tube.

In another aspect of the invention, a method for applying a plasma to an interior wall of a article comprises positioning the article in the plasma zone of the apparatus of the invention, evacuating the chambers, bleeding a gas into the chambers and delivering power to the electrodes. An electromagnetic field is formed which passes through the walls of the article and ionizes the gas inside the article to give a plasma which treats the interior wall of the article. In the preferred method, a luminal wall of a tube is treated by drawing the tube through the plasma zone.

An alternative method of the invention comprises holding the tube stationary between support rails and moving the dielectric having the electrodes disposed therein along the rails from one end of the tube to the other.

In accordance with the invention, the dielectric shields the electrodes on all sides except the facing sides so that a capacitively coupled plasma discharge is formed only in the plasma zone between the electrodes. This arrangement allows simultaneous treatment of one or more tubes, all of which receive an intense plasma generated at a relatively low power level. Only a low power is required because all external discharges which dissipate power are prevented. The low power required to generate the plasma prevents heat build-up which may cause thermal damage to polymeric materials of low softening points. By control of the pressure differential from one end of the tube to the other, the plasma is generated evenly in the plasma zone between the electrodes so that the lumen surfaces of long tubes having an inside diameter (ID) as low as 2.5 257 mm, or even lower, are uniformly modified.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

Ordinarily, a plasma discharge generated by parallel plate electrodes is directed throughout the entire region surrounding the electrodes. The apparatus of the present invention prevents any substantial discharge except that developed within a tube in the plasma zone between the electrodes. The lumen wall of a tube positioned in the plasma zone is subjected to an intense plasma because none of the power applied to the electrodes is wasted as external plasma discharge.

In accordance with the invention a glow discharge is preferred because it is a substantially "cold" plasma. The preferred apparatus generates a glow discharge plasma capacitively between parallel plate electrodes. The plasma produced is uniform and easily controlled and therefore gives uniform modification of the luminal wall of a small diameter tube. A plurality of tubes may be treated at once so that the apparatus may be used for at least semi-automated tube treatment.

Figure 1:
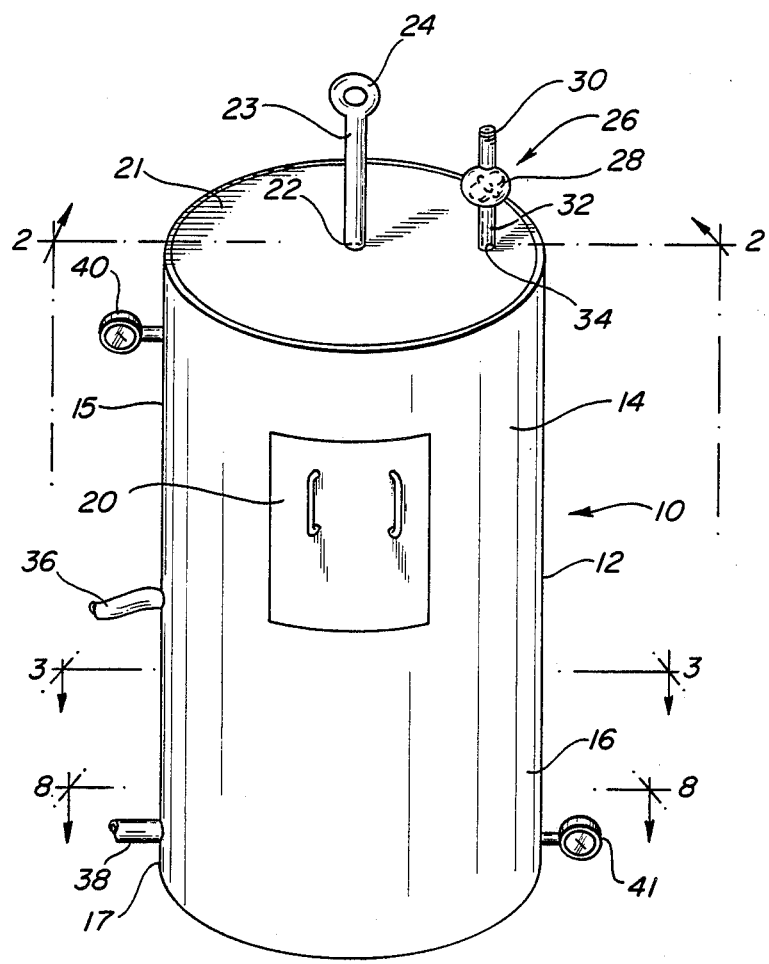
FIG. 1 is a perspective view of a preferred apparatus for plasma generation of the invention.
Figure 2:
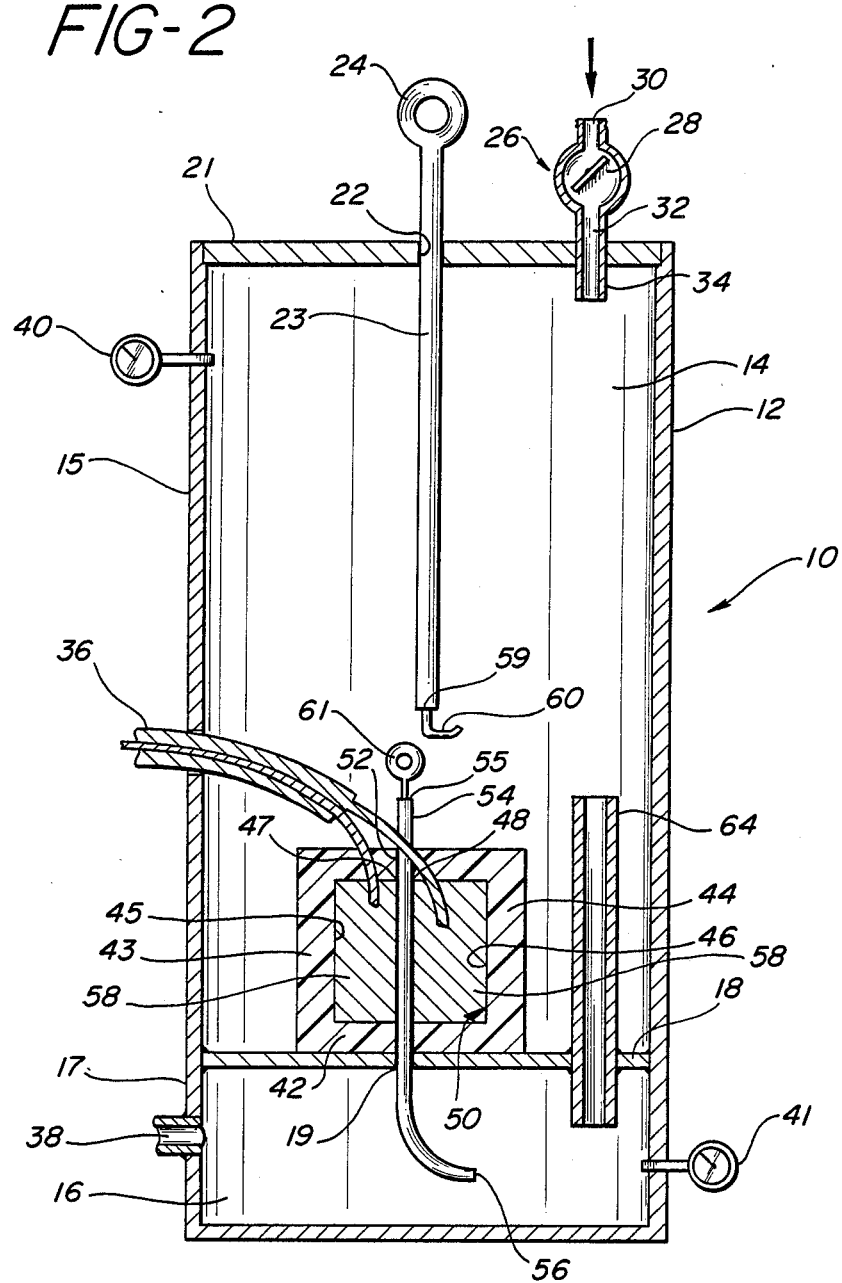
FIG. 2 is a vertical sectional view of the apparatus of FIG. 1 taken along the line 2—2 thereof.

Referring now to the drawings, FIGS. 1 and 2 show a plasma generator 10 of the invention which includes a canister 12 having an upper chamber 14 having a sidewall 15 and a lower chamber 16 having a sidewall 17. Chambers 14 and 16 are separated by a diaphragm 18 having aperture 19 therethrough. Upper chamber 14 has a door 20 which provides access to the interior of the chamber, and which may be sealingly closed when the apparatus is evacuated, as described below. A top wall 21 of upper chamber 14 has an aperture 22 therethrough. A rod 23 having a handle 24 for grasping projects sealingly and slidably into upper chamber 14 through aperture 22.

Gas inbleed 26 includes a valve 28 and a tube 30 adapted for connection to a gas source (not shown in the drawings). The gas source may be a single gas or a mixture of gases mixed in conventional apparatus prior to entry into tube 30. An inlet tube 32 connects valve 28 with upper chamber 14 and passes through port 34 in top wall 21. A coaxial cable 36 passes through side wall 15 and is connected to an RF power supply (not shown in the drawings). A nozzle 38 is affixed to lower chamber 16 and is adapted to be connected to a vacuum source (not shown in the drawings). Pressure gauges 40 and 41 are connected to upper chamber 14 and lower chamber 16, respectively.

As illustrated more clearly in FIG. 2, a dielectric 42 supported on diaphragm 18 preferably consists of two blocks 43 and 44 of high molecular weight plastic, such as polyethylene joined face to face. Recesses 45 and 46 are located in the interior of blocks 43 and 44. For example, recesses 45 and 46 may be machined out of blocks 43 and 44, or the blocks may be molded to contain the recesses. Blocks 43 and 44 also define grooves 47 and 48 such that, when blocks 43 and 44 are joined face to face, recesses 45 and 46 mate to form cavity 50 and grooves 47 and 48 mate to form bore 52 which passes through cavity 50.

Bore 52 receives, in a snug but sliding fit, a plastic tube 54 to be plasma treated. Tube 54 has a proximal end 55 and a distal end 56. Two electrodes 58 are disposed in recesses 45 and 46 in snug pressure fits. The depth of the recesses is such that when electrodes 58 are in place in the recesses, the electrodes are immediately adjacent tube 54 and define the plasma zone as that portion of bore 52 between the electrodes. Coaxial cable 36 conducts power from the RF source to electrodes 58.

Rod 23 having an internal end 59 passes through aperture 22 and extends through upper chamber 14. Preferably affixed to internal end 59 of rod 23 is a hook 60 adapted to be engaged with an eye 61 preferably attached to proximal end 55 of tube 54.

A gas flow limiting conduit 64 provides gas communication through diaphragm 18 between upper chamber 14 and lower chamber 16, as described in detail below.

Figure 3:
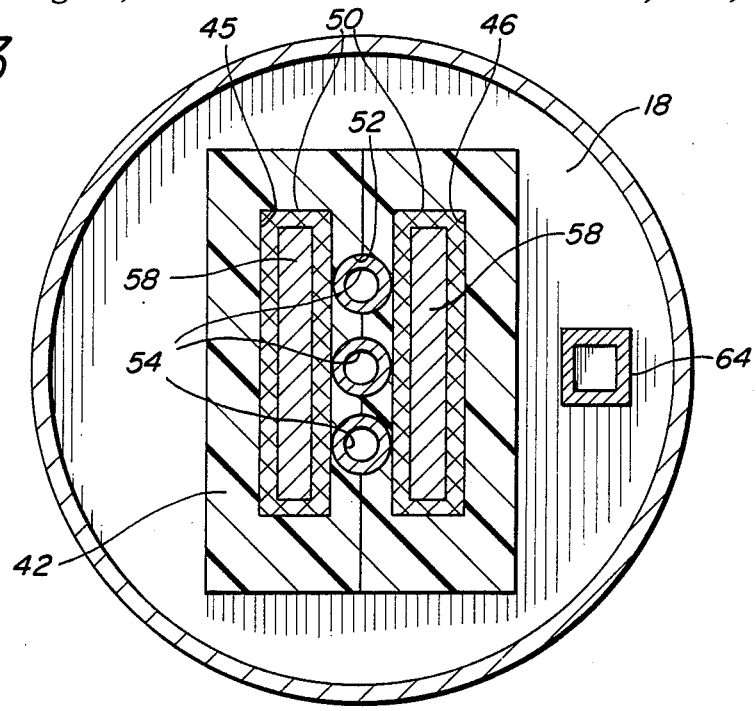
FIG. 3 is a horizontal sectional view of a portion of the apparatus of FIG. 1 taken along the line 3—3 thereof.

Details of the relationship of dielectric 42, plastic tube 54 and electrodes 58 are illustrated in FIG. 3. Electrodes 58 are shown positioned snugly in cavity 50 and flush with one or more tubes 54 in one or more bores 52, the electrodes being completely shielded by dielectric 42.

In plasma treatment of the luminal wall of small diameter tubes 54 in accordance with the invention, it is preferred, though not essential, that a pressure differential be maintained between proximal end 55 and distal end 56 of the tube. This pressure differential is preferably small enough to allow a uniform plasma to be generated at both ends of the tube yet large enough to produce a flow of the process gas through the tube and thereby purge away outgassed components from the tube. In general, for any given set of plasma parameters, a uniform plasma may be obtained in the plasma zone when a pressure differential of about 0 to 30%, preferably about 10%, is maintained between tube ends 55 and 56. Thus, for example, if the gas pressure at proximal end 55 is 14.0 torr, the preferred pressure at distal end 56 may be about 12.6 torr.

It is evident to one skilled in the art that a pressure differential may be developed between proximal and distal ends 55 and 56 by regulating the rate of gas flow through inbleed 26 and the rate of evacuation through nozzle 38 as monitored by pressure gauges 40 and 41 in upper and lower chambers 14 and 16 respectively. A preferred structure for developing and maintaining the desired pressure differential, as illustrated in FIG. 2, is the gas flow limiting conduit 64. Conduit 64 passes from upper chamber 14 to lower chamber 16 through diaphragm 18 and serves to limit the gas flow between the chambers.

Figure 4:
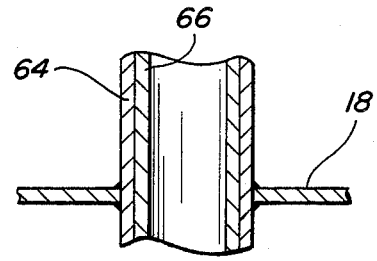
FIG. 4 illustrates in enlarged cross-section a preferred gas flow control of the apparatus of FIG. 2.

For some applications of the plasma generating apparatus of the invention, the preferred pressure differential between the chambers may be other than 10%. FIG. 4 shows a preferred means to adjust the ratio simply by inserting a sleeve 66 inside of conduit 64. Sleeve 66 may be of any wall thickness, thereby adjusting the ratio without modification of conduit 64 itself.

Figure 5:
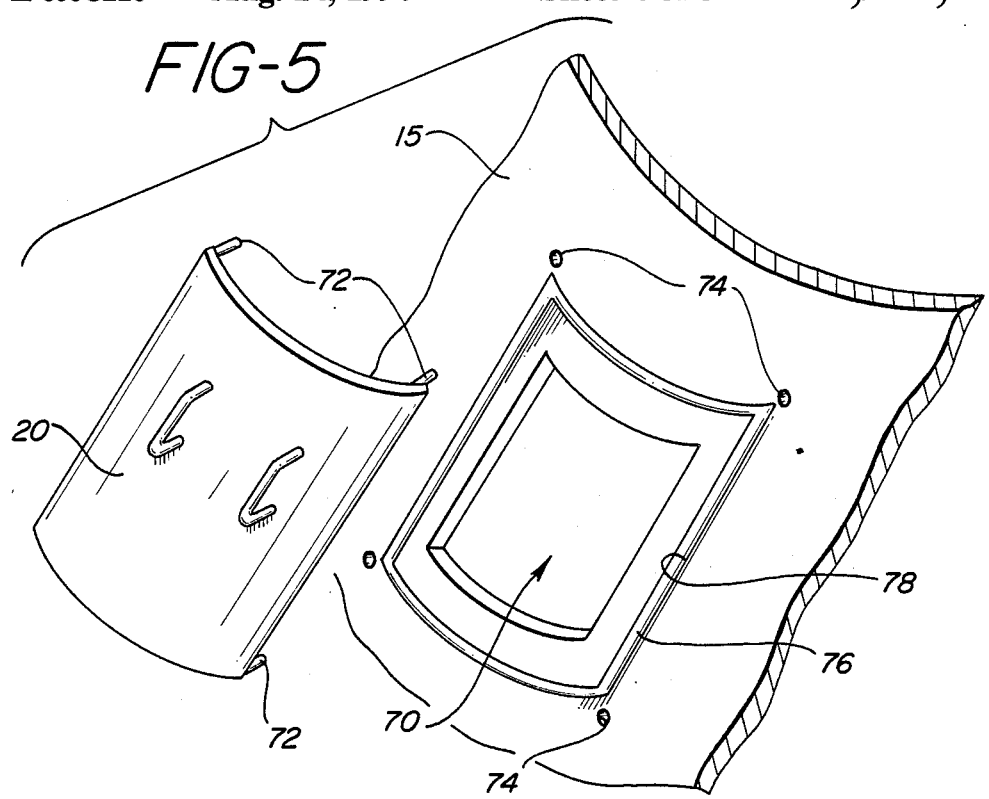
FIG. 5 is an exploded view showing the structure for opening and closing the apparatus of FIG. 1.

As mentioned above, the apparatus has structure to provide access to the interior of the canister. One suitable structure is illustrated in FIGS. 1 and 5 as door 20. FIG. 5 shows door 20 mating with an opening 70 in side wall 15 of upper chamber 14. Door 20 preferably has pegs 72 at the corners which enter slots 74 of side wall 15, the pegs thereby serving to locate door 20 over opening 70. An O ring 76 in a groove 78 of side wall 15 forms a seal with door 20 when vacuum is applied through nozzle 38.

Figure 6:
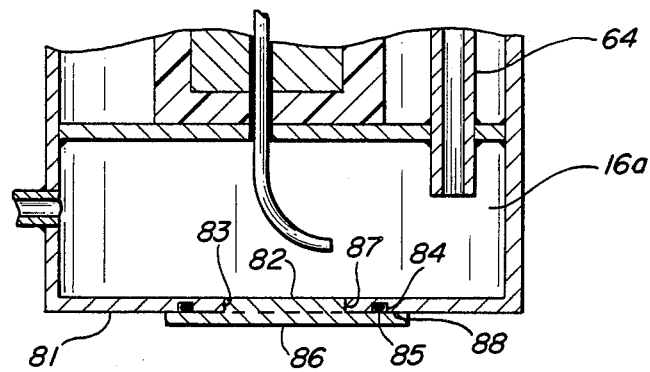
FIGS. 6 and 7 are partial vertical sectional views of the apparatus of FIG. 1 showing alternate structure for opening the apparatus.
Figure 7:
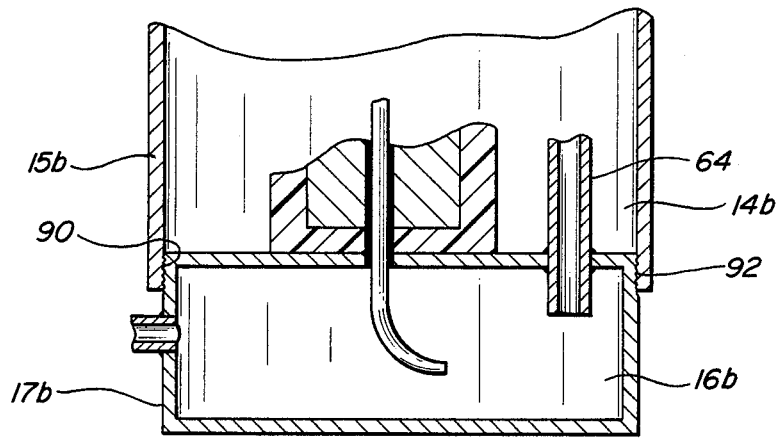

FIGS. 6–8 show structures, alternate to the door of FIG. 5, for opening canister 12. (In the following discussion of alternate embodiments of the invention, elements which correspond to elements previously described with respect to the apparatus of FIG. 1 are given the same base number followed by a lower case letter.)

In FIG. 6, bottom wall 81 of lower chamber 16a has an opening 82 and a thread 83 on the inner surface of wall 81. A groove 84 in bottom wall 81 receives an O-ring 85. Cover plate 86 has a thread 87 which mates with thread 83 whereby upper surface 88 of cover plate 86 sealingly engages O-ring 85.

As shown in FIG. 7, chambers 14b and 16b are removably affixed and sealed by mating threads 90 and 92 on side walls 15b and 17b respectively. Any conventional means for sealing the thread joint, such as grease, may be used.

Figure 8A:
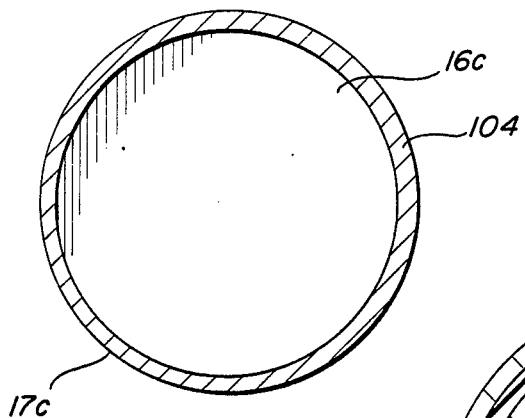
FIG. 8a is a horizontal sectional view of the apparatus of FIG. 1 taken along the line 8—8.
Figure 8B:
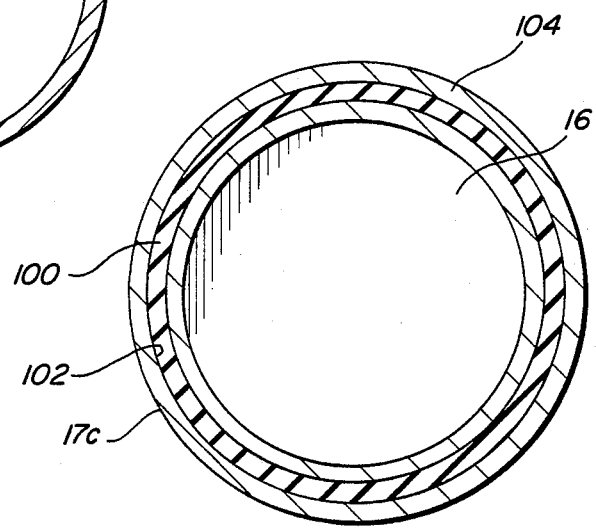
FIG. 8b is a horizontal sectional view similar to FIG. 8a, but illustrating an alternate structure for sealably opening and closing the apparatus.

The upper and lower chambers may be separable. FIG. 8a shows side wall 17c of lower chamber 16c having a flat upper surface 104. FIG. 8b illustrates an O ring 100 in a groove 102 of flat upper surface 104. O ring 100 sealingly engages the lower surface of the sidewall of the upper chamber when vacuum is applied through nozzle 38.

Structures (not shown in the drawings) other than the hook 60 and eye 61 illustrated in FIG. 2 may be used to affix rod 23 to tube 54. For example, internal end 59 of rod 23 and proximal end 55 of tube 54 may be affixed by a clamp or merely be tied together with cord or wire. Alternatively, a small magnet inserted by a pressure fit into proximal end 55 of the tube 54 may engage a piece of magnetic material attached to internal end 59 of rod 23.

Figure 9:
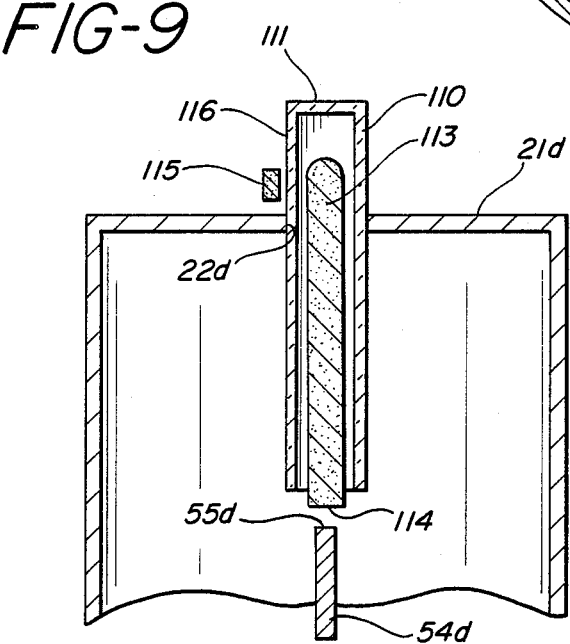
FIG. 9 is a partial vertical sectional view of a modification of the apparatus of FIG. 1 taken along the line 2—2 thereof showing an alternate structure for drawing the tube to be treated through the plasma zone.

An alternate embodiment of the invention, illustrated in FIG. 9, also uses magnetism to draw the tube through the plasma zone and at the same time eliminates the sliding seal between rod 23 and top wall 21 of FIG. 2, which may be a source of leakage. In FIG. 9, a preferably slender glass casing 110 having closed end 111 is permanently sealed into aperture 22d of top wall 21d. Rod 113, preferably of a magnetic material, or glass having magnetic bands thereon, or other magnetic material, is disposed slidably in casing 110. End 114 of rod 113 is affixed by any suitable means as described above, to proximal end 55d of tube 54d. Magnet 115, when placed on outside wall 116 of casing 110 may be slid upwardly to cause rod 113 to slide in casing 110 and draw tube 54d with it.

Figure 10:
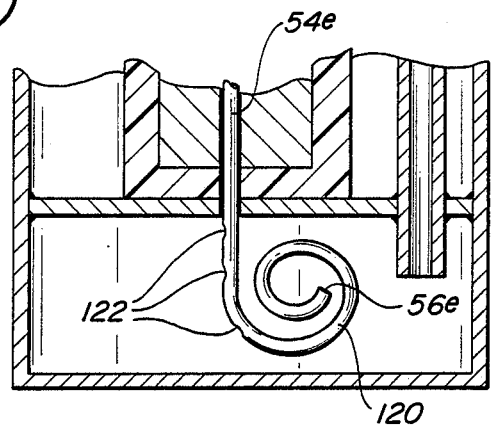
FIG. 10 is a partial vertical sectional view of the apparatus of FIG. 1 taken along the line 2—2 thereof showing a long tube ready for plasma treatment.

Any length of tube 54 may be treated with the apparatus and method of the invention. It is evident from FIG. 2 that distal end 56 may be the end of a coil of tube 54 disposed in lower chamber 16. FIG. 10 illustrates coil 120 of tube 54e having distal end 56e. Preferably coil 120 has a plurality of holes 122 spaced about 1 meter apart to aid in passage of gas through tube 54e. In this embodiment of the invention, it has been found that holes 122 preferably have a diameter substantially the same as the ID of tube 54e. When plasma treating coil 120, it is convenient to use the embodiment of the canister illustrated in FIG. 6 having access to the lower chamber for insertion of the coil.

Figure 11:
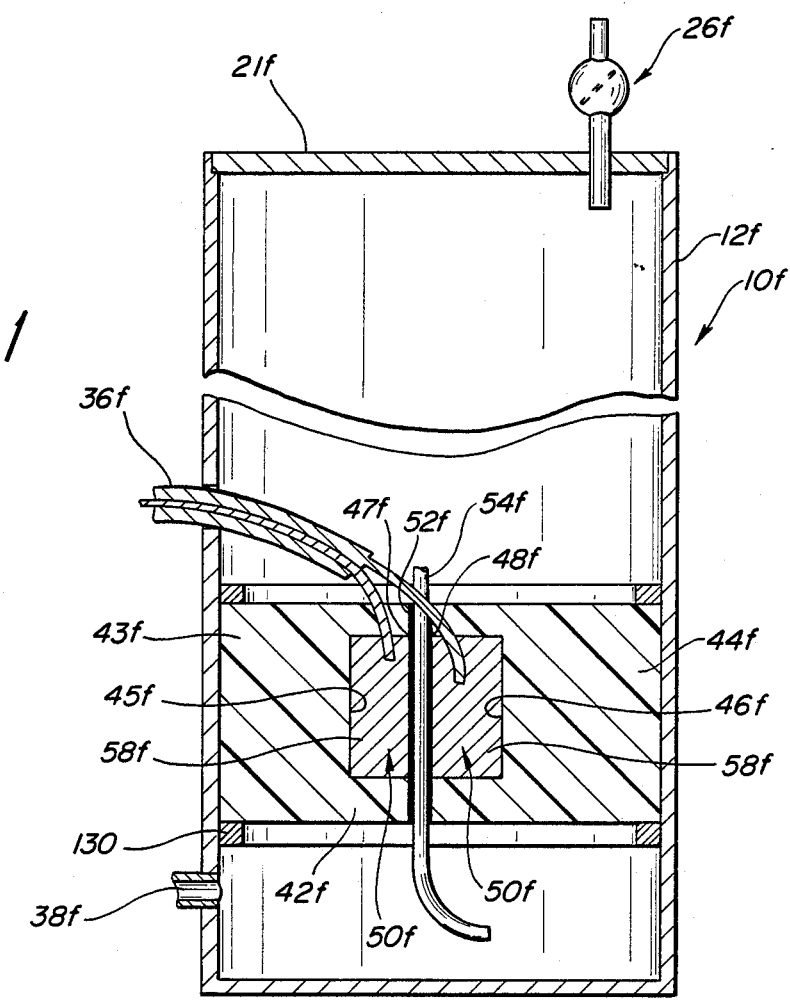
FIG. 11 is a vertical sectional view of a modification of the apparatus of FIG. 1 taken along the line 2—2 thereof showing a simplified apparatus for treating a stationary tube.

For some plasma treatments, a simplified apparatus, as shown in FIG. 11 may be suitable. It is seen that FIG. 11 is similar to the apparatus of FIGS. 1 and 2 except it lacks diaphragm 18, conduit 64, gauges 40 and 41 and the structure by which the tube is drawn through the plasma zone. In FIG. 11 plasma generator 10f includes a canister 12f having dielectric 42f supported therein on circumferential rim 130. Dielectric 42f consists of blocks 43f and 44f having recesses 45f and 46f which define cavity 50f. Grooves 47f and 48f mate to form bore 52f which receives tube 54f. Electrodes 58f are positioned in recesses 45f and 46f and define a plasma zone in bore 52f therebetween.

Figure 12:
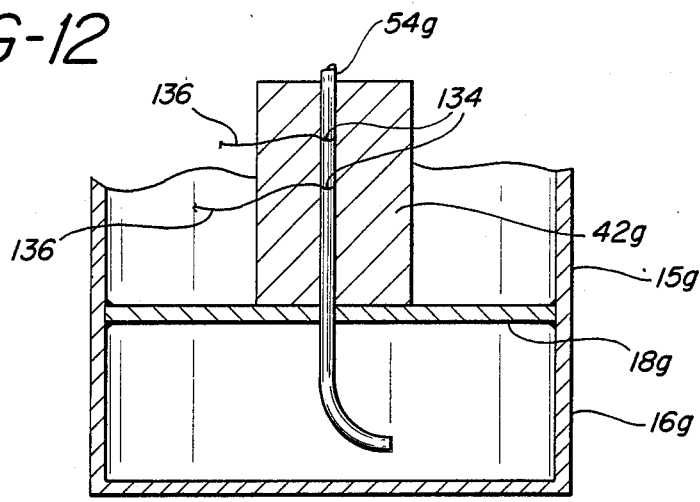
FIGS. 12 and 13 are partial vertical sectional views of the apparatus of FIG. 1 taken along the line 2—2 thereof showing a tube in position for treatment by an alternate embodiment of the generator-dielectric portion of the apparatus of the invention.

FIG. 12 shows a plurality of ring electrodes 134 around tube 54g and within dielectric 42g. Leads 136 connect ring electrodes 134 to a power source (not shown). Electrodes 134 may be spaced about 1–10, preferably about 2–5 cm apart.

Figure 13:
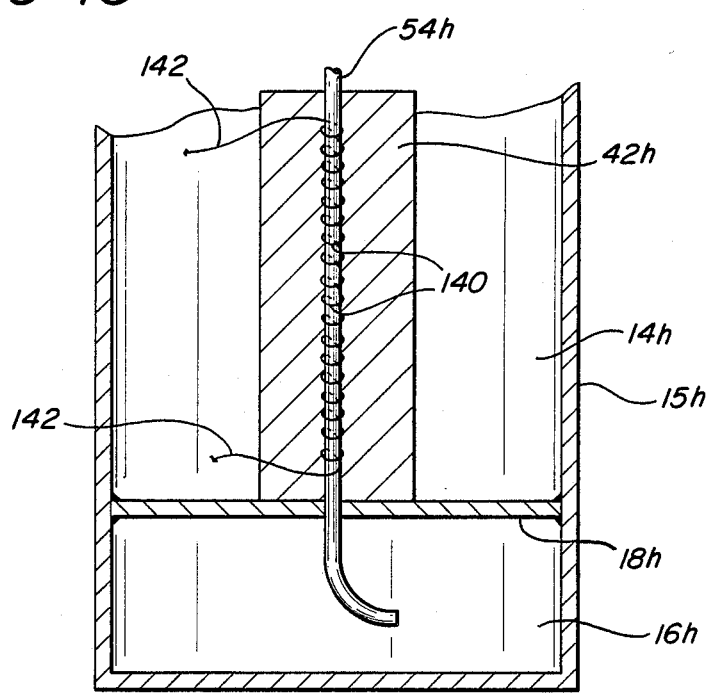

Although plasma generated capacitively between parallel plate electrodes is preferred, an inductively generated plasma may also be used to treat a luminal surface in accordance with the invention. FIG. 13 illustrates an arrangement suitable for this embodiment of the invention. Coil 140 having leads 142 connected to a power source (now shown) is wrapped around tube 54h and is completely encased in dielectric 42h.

Still other arrangements of the elements of the generator of the invention for plasma treatment of tube lumens with electrodes shielded by a dielectric may be envisioned. For example, a stationary tube may be positioned adjacent an electrode encased in a dielectric, and the electrode-dielectric unit moved past the tube to generate the plasma in the tube lumen.

Figure 14:
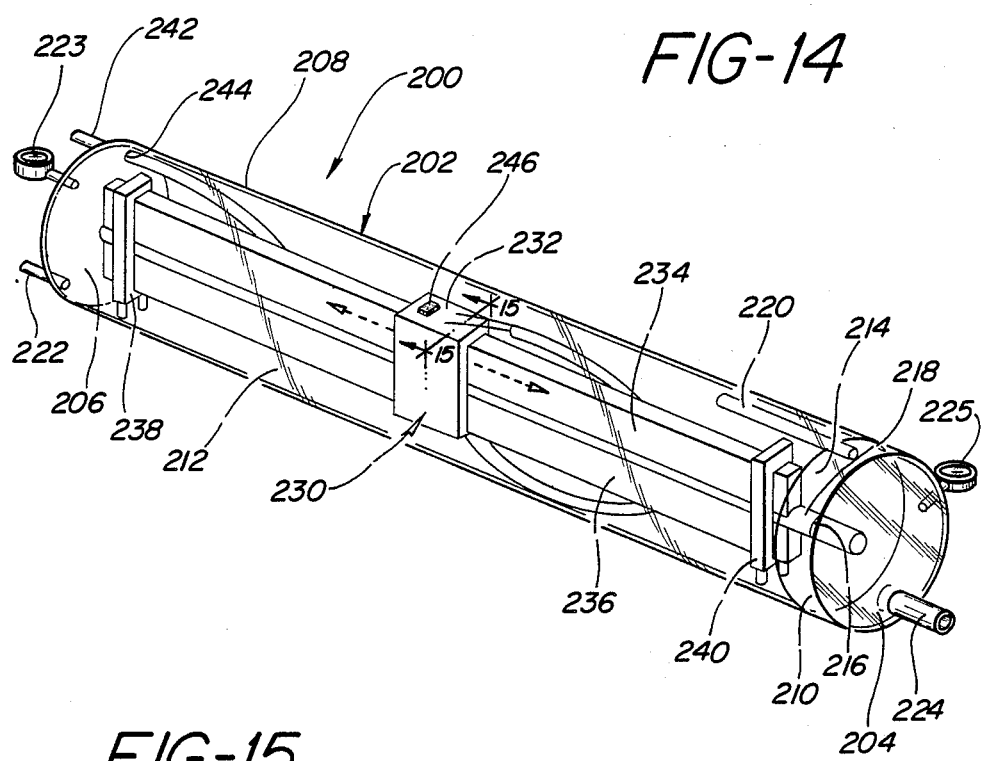
FIG. 14 is a perspective view of a preferred apparatus of the invention for generation of plasma in a long tube.
Figure 15:
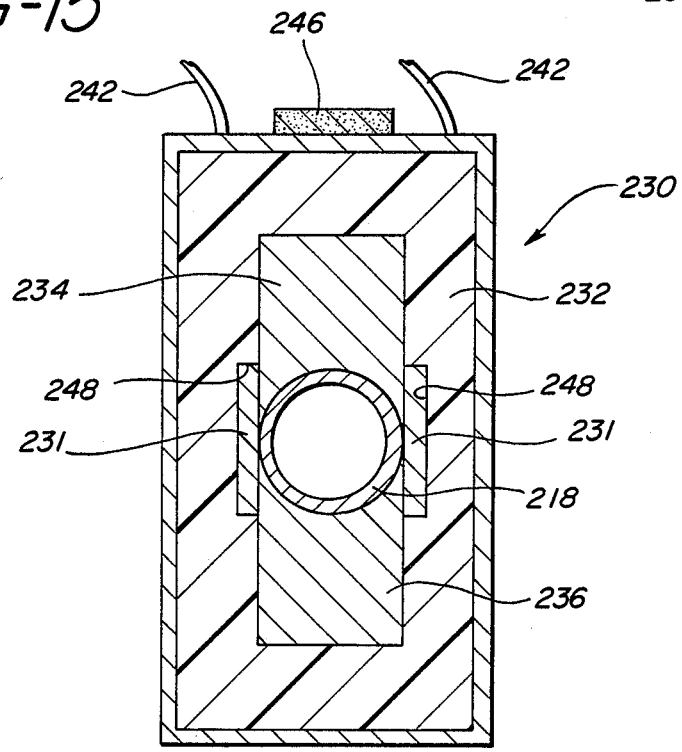
FIG. 15 is a vertical sectional view of the apparatus of FIG. 14 taken along the line 15—15 thereof.

FIGS. 14 and 15 illustrate an embodiment of the plasma generator of the invention including a moving electrode-dielectric assembly which is particularly suitable for plasma treatment of the lumen walls of long tubes. The embodiment shown in these figures is preferably disposed substantially horizontally.

A plasma generator 200 includes a housing 202, preferably cylindrical, having a proximal end plate 204, a distal end plate 206 and a side wall 208. Although housing 202 can be of any suitable material, such as metal, ceramic, plastic or glass, it will be illustrated in FIG. 14 for the preferred glass or transparent plastic so that the relationship of the internal elements may be readily visualized.

Housing 202 is divided into proximal chamber 210 and distal chamber 212 by a diaphragm 214 having a hole 216 therethrough for receiving a tube 218. A gas flow limiting conduit 220 and optional sleeves provide gas communication through diaphragm 214 as described above for conduit 64.

End plate 204 and diaphragm 214 are sealingly engaged to sidewall 208 by an suitable means, preferably by an O-ring (not shown). End plate 206 may also be sealingly engaged to sidewall 208, but preferably is integral with the sidewall.

Gas inbleed 222 and pressure gauge 223 pass through distal end plate 206. Vacuum nozzle 224 and pressure gauge 225 pass through proximal end plate 204, all forming vacuum tight seals with their respective end plates.

Removably positioned within distal chamber 212 is an electrode-dielectric assembly 230 including electrodes 231, dielectric 232, upper tube support rail 234, lower tube support rail 236, distal clamp 238 and proximal clamp 240. Coaxial cable 242 passes sealingly through hole 244 in distal end plate 206 and delivers RF power to the electrodes. Magnet 246 is secured to dielectric 232 by any suitable means, as for example glue.

As shown in FIG. 15, electrodes 231 fit snugly in cavities 248 in dielectric 232, as described above for electrodes 58. Tubing 218 is positioned between upper rail 234 and lower rail 236 in the plasma zone immediately adjacent electrodes 231. Assembly 230 is adapted for withdrawal from housing 202 for insertion of tube 218 as described below.

All embodiments of the apparatus of the invention as heretofore described may be used with a conventional high frequency RF generator and impedance matching network and a conventional vacuum system. Such equipment is well known in the art (as, for example, in U.S. Patent No. 3,847,652) and further details with respect to these aspects of the invention are not needed for a complete understanding of the invention.

In preparation of generator 10 for use, canister 12 is opened and tube 54 to be plasma-treated is inserted into bore 52 so that it occupies the plasma zone between electrodes 58. Eye 61 is attached to proximal end 55 of the tube by any suitable means. Hook 60 on internal end 59 of rod 23 is engaged with eye 61, and the canister 10 is sealingly closed.

Inserting a tube into generator 200 may be carried out by removing proximal end plate 204 and diaphragm 214 from housing 202 and sliding assembly 230 forward until completely removed from housing 202. Clamps 238 and 240 are opened and removed, and dielectric 232 is slid over upper and lower rails 234 and 236 until disengaged therefrom. The rails are then separated and a tube 218 to be plasma treated is placed therebetween. The generator is then reassembled by reversing these steps.

For plasma treatment of the tube, the loaded and assembled generator 10 or 200 is evacuated by attaching the vacuum nozzle to a vacuum pump. Gas from a gas source is bled into the evacuated apparatus through the gas inbleed until the desired gas pressure differential across the conduit is obtained. As mentioned above, one or more sleeves may be inserted into the conduit if it is desired to reduce the diameter of the conduit. An RF electromagnetic field is generated in the plasma zone by applying current of the desired frequency to the electrodes from the RF generator. Ionization of the gas in the tube is induced by the field, and the resulting plasma in the tube modifies the luminal wall of the section of tube in the plasma zone.

If it is contemplated to plasma treat a length of tube equivalent to or less than the length of the electrodes, an apparatus in accordance with FIG. 11 may preferably be used. If the length of tube to be treated is greater than the length of the electrodes, the entire tube may be treated with the apparatus of FIG. 10 or, preferably, with the apparatus of FIG. 14. An external magnet (not shown in FIG. 14) is placed directly above magnet 246 on the outside of side wall 208. The two magnets are thereby magnetically engaged so that lateral movement of the external magnet along the side wall causes the dielectric-electrode unit to slide along the rails in either direction, as shown by the dotted arrows in FIG. 14. Determination of a suitable rate for drawing the tube of FIG. 10 or the electrode-dielectric unit of FIG. 14 to give the desired degree of surface modification is well within the purview of one skilled in the art.

The apparatus and method of the invention may be used to treat a luminal surface with a plasma generated from any gas under any suitable plasma parameters to be determined in accordance with the desired surface treatment. Thus, without wishing to be limited thereby, the gas may be ammonia, nitrogen, neon, argon, xenon, krypton, oxygen or mixtures thereof. In addition, the gas may be a vaporized organic material, such as an ethylenic monomer or a lower molecular weight siloxane to be plasma polymerized or deposited on the luminal wall of the tube.

Suitable plasma parameters may be power levels from about 10 to 1000 watts, RF frequency of about 1 to 100 meqaherz, exposure times of about 5 seconds to 12 hours, gas pressures of about 0.1 to 100 torr and a gas flow rate of about 1–200 standard cc/sec.

In accordance with the method of the invention in which a small diameter conduit is plasma treated to modify the luminal wall in preparation for attachment of endothelial cells, a preferred plasma is generated using the apparatus of the invention from ammonia or nitrogen with a power level of 50–125 watts, an RF frequency of about 8—30 megaherz, an exposure time for a particular area of the tube of about 0.2 to 2.0 min., a gas pressure of about 1–20 torr and gas flow rate of about 5 to 20 standard cc/sec.

Dielectrics 42 and 232 may be of any material which prevents the electromagnetic field from being applied in any direction other than into the plasma zone between the electrodes. Suitable materials are, for example, glass, rubber, ceramic and, preferably, a high molecular weight polyolefin such as polypropylene or polyethylene. It has been found that when the electrodes are encased with about 1 to 5, preferably about 2 ½ cm of dielectric material, sufficient shielding is provided so that substantially no plasma is formed external of the plasma zone.

Suitable electrodes may be of any conducting material, although aluminum and stainless steel are preferred. Preferred electrodes are from 2 to 10 cm long although any length consistent with the dimensions of the housing are suitable. Likewise, the width and height of the electrodes are not critical, although preferred electrodes are about 0.1 cm in thickness and about 0.5 to 2.0 cm in width.

As mentioned above, housing 202 may be metal, plastic or, preferably, glass. It is of course understood by one skilled in the art that a metal housing must be non-ferrous when magnets are to be used to move the electrodes. The tube support rails may likewise be glass or plastic, preferably a plastic having a low friction surface.

While the apparatus of the invention has been described in detail for the plasma treatment of the lumen of a small diameter tube, it is apparent that merely by altering the dimensions of the dielectric and the electrodes, any article having an internal surface which can be contacted with a plasma gas can be treated. The article to be plasma-treated may be of any non conducting material such as glass, plastic, ceramic, rubber and composites thereof. Conducting materials such as metals cannot be treated on internal surfaces with the apparatus of the invention because electromagnetic fields do not pass through conductors. A preferred material for a vascular graft is polyurethane because its high degree of compliance and flexibility makes it most similar to a human blood vessel.

Thus, the apparatus of the invention generates a plasma in the lumen of a tube as small as 2.5 mm ID, or even smaller. The plasma is generated in a plasma zone between electrodes shielded by a dielectric which prevents substantially all plasma generation external to the plasma zone. By limiting plasma generation to the plasma zone, no power is wasted so that the desired plasma is generated inside of the tube in the plasma zone without application of excessive power to the electrodes. As a result, heat buildup is minimized allowing plasma treatment of the luminal wall of a tube made of a heat sensitive material.

What is claimed is:

1. A method for treating a luminal wall of a tube with a plasma comprising:
   (a) positioning a tube in a plasma zone adjacent a plurality of electrodes, said electrodes being encased in a dielectric in a housing enclosing two chambers separated by a diaphragm and connected by a conduit;
   (b) evacuating a first of said chambers;
   (c) bleeding a gas into a second of said chambers, said gas contacting a luminal wall of said tube;
   (d) regulating a pressure differential between the proximal and distal ends of said tube with said conduit; and
   (e) delivering radiofrequency power to said electrodes, said power developing an electromagnetic field, said field ionizing said gas in contact with said luminal wall, said ionizing causing a plasma, said plasma treating said luminal wall.

2. The method in accordance with claim 1 further comprising drawing said tube through said plasma zone.

3. The method in accordance with claim 1 further comprising moving said dielectric having said electrodes encased therein past said tube in said plasma zone.

* * * * *